(12) United States Patent
Kang et al.

(10) Patent No.: US 9,309,172 B2
(45) Date of Patent: Apr. 12, 2016

(54) METHOD FOR SEPARATING ETHYLENE OR ETHANE FROM MIXED GAS

(71) Applicant: Korea Institute of Energy Research, Daejeon (KR)

(72) Inventors: Seong-Pil Kang, Daejeon (KR); Jong-Won Lee, Chungcheongnam-do (KR); Dongwook Lee, Daejeon (KR); Yong Koo Kim, Daejeon (KR)

(73) Assignee: Korea Institute of Energy Research, Daejeon (KR)

( * ) Notice: Subject to any disclaimer, the term of this patent is extended or adjusted under 35 U.S.C. 154(b) by 348 days.

(21) Appl. No.: 14/160,631

(22) Filed: Jan. 22, 2014

(65) Prior Publication Data

US 2014/0206920 A1    Jul. 24, 2014

(30) Foreign Application Priority Data

Jan. 24, 2013    (KR) ........................ 10-2013-0007902

(51) Int. Cl.
*C07C 7/152*    (2006.01)
*C07C 7/14*    (2006.01)
(52) U.S. Cl.
CPC ..................................... *C07C 7/152* (2013.01)
(58) Field of Classification Search
CPC ................................. C07C 7/14; C07C 7/152
USPC ............................................ 585/15, 809, 833
See application file for complete search history.

(56) References Cited

U.S. PATENT DOCUMENTS 4,218,229 A * 8/1980 Schuster .................. C07C 7/04
62/623

\* cited by examiner

*Primary Examiner* — Thuan D Dang
(74) *Attorney, Agent, or Firm* — Dority & Manning, P.A.

(57) ABSTRACT

The present invention provides a method of separating ethylene or ethane from a mixed gas containing ethylene and ethane using hydroquinone. According to the present invention, hydroquinone selectively forms a clathrate with ethylene, and thus it is possible to separate ethylene with high yield and purity through a single process.

6 Claims, No Drawings

METHOD FOR SEPARATING ETHYLENE OR ETHANE FROM MIXED GAS

CROSS-REFERENCE TO RELATED PATENT APPLICATION

This application claims the benefit of Korean Patent Application No. 10-2013-0007902, filed on Jan. 24, 2013, in the Korean Intellectual Property Office, the disclosure of which is incorporated herein in its entirety by reference.

BACKGROUND OF THE INVENTION

1. Field of the Invention

The present invention relates to a method for selectively separating ethylene from a mixed gas by forming an ethylene-hydroquinone clathrate.

2. Description of the Related Art

When the catalytic pyrolysis of naphtha is performed, various types of gases are generated, which are then separated and recovered, respectively, to obtain various necessary components. The main components of naphtha pyrolysis gas include hydrogen, nitrogen, methane, ethane, ethylene, propane, propylene, carbon dioxide, etc. Among these components, most hydrocarbons have low boiling points and are not easily separated because of their close boiling points. There are several methods developed to separate the hydrocarbons, but it can be said that deep freezing distillation is almost the only method currently available that is economically feasible and can provide high throughput.

However, even with the use of the deep freezing distillation, it is not easy to separate ethylene contained in the pyrolysis gas. In general, the method for recovering ethylene from the pyrolysis gas begins by separating C4+ hydrocarbons having relatively high boiling points, and then has a step for separating C1 hydrocarbon (methane) and hydrogen. The separation of C2 and C3 hydrocarbons is the final stage of the recovery process. Among these steps, it is very difficult to separate ethane and ethylene because of their small differences in relative volatilities.

Ethylene is the smallest unit of hydrocarbons containing a double bond and is the major product of the petrochemical industry. Various copolymers can be produced by polymerization using the double bond of ethylene or reaction between the double bond of ethylene and other substances, and thus its application is very wide in petrochemical industry. As a result, it is necessary to develop a method for effectively and economically separating effective substances such as ethane and ethylene from the pyrolysis gas. Therefore, a significant improvement in process productivity and economics is expected when yield and efficiency of the process are improved and energy consumption is reduced even by a small margin compared to the conventional deep freezing distillation, considering the scale of the process.

SUMMARY OF THE INVENTION

Accordingly, an object of the present invention is to provide a method for separating ethylene or ethane from a mixed gas by forming an ethylene-hydroquinone clathrate by bringing a mixed gas containing ethane and ethylene into contact with hydroquinone.

An aspect of the present invention is to provide a method for separating ethylene or ethane from a mixed gas containing ethylene and ethane by forming a clathrate using hydroquinone represented by the following Chemical Formula 1:

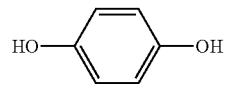

[Chemical Formula 1]

Clathrate is a kind of inclusion compound and refers to a stable crystal produced in a manner that gas molecules of low molecular weight such as methane, carbon dioxide, nitrogen, etc. are physically bonded to cavities formed by host molecules under high-pressure and low-temperature conditions in general. In particular, when the host molecules are water, it is called "gas hydrate", and when the host molecules are organic materials, it is called "clathrate", respectively.

Hydroquinone can form hydrogen bonds with each other by OH groups at both ends of a benzene ring and can form the clathrate under appropriate temperature and pressure conditions. According to the chemical formula, one guest molecule is bonded to three molecules of hydroquinone.

The hydroquinone forms the clathrate with ethylene. Therefore, the hydroquinone can selectively form the clathrate with ethylene in a mixed gas containing ethylene preferentially over other types of gases, allowing ethylene to be effectively separated from the mixed gas.

The method of the present invention includes forming an ethylene-hydroquinone clathrate by bringing a mixed gas containing ethane and ethylene into contact with hydroquinone; and thus separating ethylene from the clathrate.

According to the above method, ethylene can effectively form the clathrate with hydroquinone, among the pyrolysis gas components. As a result, when hydroquinone is brought into contact with the mixed gas containing ethylene and ethane, ethylene can selectively form the clathrate with hydroquinone, which thus makes it possible to effectively remove ethylene from the mixed gas and to obtain ethylene from the clathrate by dissociating the formed clathrate.

Moreover, when ethylene forms the clathrate with hydroquinone and is removed from the mixed gas, the content of ethane increases in the mixed gases remarkably, which makes it possible to more easily and effectively separate ethane from the mixed gas, thus selectively obtaining ethane.

In general, in the case of the mixed gas containing both ethane and ethylene, The boiling points of ethane and ethylene are very similar to each other, and thus it is difficult to separate ethane and ethylene by distillation and the efficiency in cost and energy is quite low. As a result, the ethylene-ethane separation process requires repetitive unit operations even when deep freezing distillation is applied in order to obtain a high purity gas containing ethylene.

Moreover, in the case of a method for separating ethylene from the mixed gas containing ethylene and ethane using hydrate formation by brining the mixed gas into contact with water, the cage occupancies at which ethane and ethylene form hydrate with water, respectively, are nearly similar to hydrate, and thus it is necessary to repeatedly perform the hydrate formation and dissociation process, making it impossible to effectively and economically separate ethane and ethylene.

However, according to the method of the present invention, ethylene in the mixed gas can selectively form clathrate with hydroquinone, and thus it is possible to separate ethylene from the mixed gas containing ethylene and ethane at a high yield. Moreover, this method can form the clathrate by simply bringing the mixed gas containing ethane and ethylene into contact with hydroquinone, and thus it is possible to separate ethylene and ethane by the simple method through a single process, which is more economical than the distillation method.

According to embodiments of the present invention, the mixed gas may be a pyrolysis gas of naphtha. During a pyrolysis reaction in which naphtha is used as a raw material and a catalyst is used, various types of gases are generated, and the gases contain ethylene. Therefore, when the pyrolysis gas is brought into contact with hydroquinone at appropriate condition and stage, it is possible to easily obtain ethylene at a significantly higher yield than the conventional distillation method, thus providing economic benefits.

According to embodiments of the present invention, the mixed gas may contain ethane and ethylene in an amount of about 40 to about 100% NM with respect to the total volume of the mixed gas, preferably 60 to 100% (v/v), more preferably 80 to 100% (v/v). In general, among various components contained in the pyrolysis gas, ethane and ethylene have similar boiling points and thus may not be completely separated even by repeated distillation with a large number of trays, but may be present in a mixed state. According to the present invention, it is possible to effectively separate ethylene and ethane in the mixed gas including ethylene and ethane. The process of the present invention allows ethylene to selectively form the clathrate with hydroquinone in the pyrolysis gas including large amounts of ethane and ethylene.

According to embodiments of the present invention, the volume ratio of ethane to ethylene contained in the mixed gas may be about 20:1 to about 1:20, about 15:1 to about 1:15, about 10:1 to about 1:10, or about 5:1 to about 1:5.

Hydroquinone does not form the clathrate with ethane, but selectively forms the clathrate with ethylene, and thus the efficiency of ethylene separation is very high. Therefore, even in the case where the mixed gas contains a very small amount of ethylene or ethane, it is possible to selectively separate ethylene at a high purity. According to the method of the present invention, it is possible to obtain a gas containing ethylene at a purity of about 90% (v/v) or higher, preferably about 95% v/v) or higher, more preferably about 98% (v/v) or higher, most preferably about 99% (v/v) or higher.

According to embodiments of the present invention, the mixed gas may further include hydrogen, pentane, pentene, hexane, benzene, heptane, toluene, octane, xylene, or a mixture thereof. The pyrolysis gas generated during the pyrolysis of naphtha may contain such types of gases. Even after predetermined types of gases are separated by various methods such as distillation, etc., the pyrolysis gas may further comprise various types of gases including compounds of C4+ and ethane or ethylene.

According to the present invention, even in the case where the mixed gas comprises these various types of gases, hydroquinone can selectively form a bond with ethylene, and thus it is possible to easily obtain ethylene at a high purity.

According to embodiments of the present invention, in the step of forming the clathrate, the mixed gas containing ethane and ethylene may be brought into contact with hydroquinone at a pressure of about 10 to about 60 atm and at a temperature of about 0 to about 30° C., preferably at a pressure of about 10 to about 60 atm and at a temperature of about 3 to about 27° C., more preferably at a pressure of about 20 to about 40 atm and at a temperature of about 4 to about 25° C. Hydroquinone selectively forms the clathrate with ethylene at the above-described temperature and pressure, but does not form the clathrate with the ethane. Therefore, ethylene can be selectively removed from the mixed gas at the above-mentioned temperature and pressure.

The above-mentioned temperature is in a room temperature environment of about 0 to 30° C., which is higher about 30 to 60° C. than the temperature of about −35° C. at which the conventional distillation method is performed. Thus, when the mixed gas and hydroquinone are left at the above-mentioned temperature and pressure, the clathrate can be formed, which is significantly meaningful in cost and energy of the process.

According to embodiments of the present invention, in the step of separating ethylene from the clathrate, the clathrate may be placed in an environment where the pressure is about 10 atm or less, or the temperature exceeds 30° C. When the clathrate is left in an environment outside the pressure or temperature condition under which the hydroquinone forms the clathrate with ethylene, ethylene trapped in the clathrate is dissociated and only solid-phase hydroquinone is left, which makes it possible to easily obtain a gas containing ethylene at a high purity.

When the clathrate is placed in an environment where the pressure is about 10 atm or less, ethylene is separated from the clathrate, and thus it is possible to obtain a gas containing ethylene at a high purity. Moreover, when the temperature is increased above about 30° C. at a pressure of about 10 atm or less, ethylene can be separated from the clathrate at a higher rate, and thus it is possible to recover ethylene at a higher rate. The step of separating clathrate of the present invention may be performed at a pressure of about 5 atm or less, preferably about 4 atm or less, more preferably about 1 atm or less.

According to the method of the present invention, the clathrate is formed by bringing the mixed gas containing ethane and ethylene into contact with hydroquinone, and thus it is possible to effectively obtain ethylene and ethane through a single step. Therefore, the process of the present invention is simpler than the conventional distillation method for obtaining ethylene through multiple stage process and can obtain ethylene with high purity and yield, and thus the process of the present invention becomes significantly economical.

For example, when hydroquinone and the mixed gas containing ethane and ethylene are injected into a reactor and the mixture is left in the reactor for a predetermined time after adjusting the temperature and pressure of the reactor to about 0 to about 30° C. and about 10 to about 60 atm, ethylene and hydroquinone can form the clathrate. As ethylene is trapped in the clathrate, the pressure of the reactor is reduced, and when the pressure reduction does not occur any longer, it can be considered that all ethylene capable of being trapped has been trapped in the clathrate.

At this time, when the pressure of the reactor is reduced below about 10 atm by pulling out the mixed gas remaining in the reactor, the clathrate is dissociated into hydroquinone and gas phase, and thus a gas containing ethylene can be obtained at a high purity. Meanwhile, ethane can be easily obtained from the remaining mixed gas in the reactor by the conventional distillation method, etc. because ethylene having a boiling point similar to that of ethane has been removed beforehand.

DETAILED DESCRIPTION OF THE INVENTION

Hereinafter, the present invention will be described in more detail with reference to the following Examples. However, the following Examples are set forth to more easily understand the present invention, and the scope of the present invention is not limited thereto.

1. Providing an Experimental System

A high-pressure reactor having an inner volume of about 350 cc and made of 316 stainless steel was provided. The high-pressure reactor was immersed in a water bath that is connected to an chiller outside to control its temperature. A sapphire window was installed in an upper part of the high-pressure reactor in order to observe the formation of clathrate, and a pressure transducer and a thermocouple were provided in the high-pressure reactor to measure the temperature and pressure of the reactor.

This experimental system including the high-pressure reactor, the water bath and devices for measuring temperature and pressure is disclosed in detail in our previous paper entitled "Hydrate phase equilibria of the guest mixtures containing $CO_2$, $N_2$ and tetrahydrofuran (Fluid Phase Equilibria 185 (2001), 101-109)".

2. Experimental Example 1

Formation of Hydroquinone and Ethane Clatharate

About 200 cc of hydroquinone was loaded into the high-pressure reactor provided in the above section 1. The high-pressure reactor was placed in a water bath capable of controlling temperature. Then, air remaining in the high-pressure reactor was removed by evacuation and ethane was injected into the high-pressure reactor until the pressure in the high-pressure reactor reached about 30 atm. Subsequently, a change in the pressure of the reactor was observed while maintaining the temperature of reactor at about 25° C. for about 3 hours.

The change in the pressure of the high-pressure reactor was not observed for 3 hours. Therefore, It was confirmed that ethane did not form the clathrate with hydroquinone.

3. Experimental Example 2

Formation of Hydroquinone and Ethylene Clathrate (1)

About 200 cc of hydroquinone was loaded into the high-pressure reactor at about 25° C. and about 1 atm, provided in the above section 1. The high-pressure reactor was placed in a water bath capable of controlling temperature, and air remaining in the high-pressure reactor was removed by evacuation. Ethylene was then injected into the high-pressure reactor until the pressure in the high-pressure reactor reached about 30 atm. Subsequently, a change in the pressure of the reactor was observed while maintaining the temperature and pressure of reactor at about 25° C. and about 30 atm for about 3 hours.

After about 3 hours, the pressure in the reactor was reduced to 26 atm. This means that ethylene formed the clathrate with hydroquinone.

Subsequently, pressure of the reactor was decreased to atmospheric condition by flushing out the remaining gas, and the temperature in the high-pressure reactor was controlled to about 50° C. so as to dissociate the hydroquinone clathrate. After the reactor was left at about 50° C. and 1 atm for 1 hour, the dissociated gas in the high-pressure reactor was collected and analyzed by chromatography, confirming that the gas was ethylene.

4. Experimental Example 3

Formation of Hydroquinone and Ethylene Clathrate (2)

About 200 cc of hydroquinone was loaded into the high-pressure reactor at about 25° C. and about 1 atm, provided in the above section 1. The high-pressure reactor was placed in a water bath capable of controlling temperature, and air remaining in the high-pressure reactor was removed by evacuation. A mixed gas of ethane and ethylene at a volume ratio of about 1:1 was then injected into the high-pressure reactor until the pressure in the high-pressure reactor was reached about 30 atm. Subsequently, a change in the pressure of the high-pressure reactor was observed while maintaining the temperature and pressure of reactor at about 25° C. and about 30 atm for about 3 hours.

After about 3 hours, the pressure in the reactor was reduced to about 28 atm. This means that the gas in the high-pressure reactor formed the clathrate with hydroquinone.

Subsequently, pressure of the reactor was decreased to atmospheric condition by flushing out the remaining gas and the temperature in the high-pressure reactor was controlled to about 50° C. so as to dissociate the hydroquinone clathrate. After the reactor was left at about 50° C. and about 1 atm for 1 hour, the dissociated gas in the high-pressure reactor was collected and analyzed by chromatography, confirming that about 98.8% (v/v) of the collected gas was ethylene.

This indicated that ethylene dominantly formed the clathrate with hydroquinone.

5. Experimental Example 4

Formation of Hydroquinone and Ethylene Clathrate (3)

About 200 cc of hydroquinone was loaded into the high-pressure reactor at about 25° C. and about 1 atm, provided in the above section 1. The high-pressure reactor was placed in a water bath capable of controlling temperature, and air remaining in the high-pressure reactor was removed by evacuation. A mixed gas of ethane, ethylene, methane, and hydrogen at a volume ratio of about 3.76:53.02:40.72:2.5 was then injected into the high-pressure reactor until the pressure in the high-pressure reactor was reached about 30 atm. Subsequently, a change in the pressure of the high-pressure reactor was observed while maintaining the temperature and pressure of reactor at about 4° C. and about 30 atm for about 3 hours.

After 3 hours, the pressure in the reactor was reduced to about 16.4 atm. This means that the gas included in the high pressure reactor formed the clathrate with hydroquinone.

Subsequently, pressure of the reactor was decreased to atmospheric condition by flushing out the remaining gas and the temperature in the high-pressure reactor was controlled to about 50° C. so as to dissociate the hydroquinone clathrate. After the reactor was left at about 50° C. and about 1 atm for about 1 hour, the dissociated gas in the high-pressure reactor was collected and analyzed by chromatography, confirming that the collected gas contained ethane, ethylene, methane, and hydrogen at a volume ratio of about 0.34:94.37:5.27:0.02 (v/v). It was confirmed that a gas containing ethylene was obtained at a high purity.

This indicated that ethylene dominantly formed the clathrate with hydroquinone.

The present invention provides a method for effectively separating ethane and ethylene through a single process of forming an ethylene-hydroquinone clathrate so as to separate ethane and ethylene from a mixed gas containing ethane and ethylene.

What is claimed is:

1. A method for separating ethylene or ethane, comprising:
   forming an ethylene-hydroquinone clathrate by bringing a mixed gas containing ethane and ethylene into contact with hydroquinone; and
   separating ethylene from the clathrate.

2. The method of claim 1, wherein the mixed gas is a pyrolysis gas generated by pyrolysis of naphtha.

3. The method of claim 1, wherein the total volume of ethane and ethylene in the mixed gas is about 40 to about 100% (v/v).

4. The method of claim 1, wherein the volume ratio of ethane to ethylene in the mixed gas is about 20:1 to about 1:20.

5. The method of claim 1, wherein the mixed gas further contains at least one more gas component selected from the group consisting of hydrogen, nitrogen, methane, propane, propylene, and carbon dioxide.

6. The method of claim 1, wherein in the forming of the clathrate, the mixed gas containing ethane and ethylene is brought into contact with hydroquinone at a pressure of about 10 to about 60 atm and at a temperature of about 0 to about 30° C.

* * * * *